(12) United States Patent
Hartmann-Thompson (10) Patent No.: US 7,799,276 B2
(45) Date of Patent: Sep. 21, 2010

(54) FUNCTIONALIZED PARTICLES FOR COMPOSITE SENSORS

(75) Inventor: Claire Hartmann-Thompson, Midland, MI (US)

(73) Assignee: Michigan Molecular Institute, Midland, MI (US)

( * ) Notice: Subject to any disclaimer, the term of this patent is extended or adjusted under 35 U.S.C. 154(b) by 2057 days.

(21) Appl. No.: 10/694,027

(22) Filed: Oct. 27, 2003

(65) Prior Publication Data

US 2005/0090015 A1    Apr. 28, 2005

(51) Int. Cl.
*G01N 33/00* (2006.01)
(52) U.S. Cl. .......................... 422/83; 422/68.1; 422/99
(58) Field of Classification Search .................. 422/83, 422/68.1, 99
See application file for complete search history.

(56) References Cited

U.S. PATENT DOCUMENTS

| | | | |
|---|---|---|---|
| 5,106,922 A | 4/1992 | Saito et al. | |
| 5,928,729 A | 7/1999 | Derosa | |
| 5,932,231 A | 8/1999 | LeGrow et al. | |
| 6,048,457 A * | 4/2000 | Kopaciewicz et al. | 210/321.6 |
| 6,315,956 B1 | 11/2001 | Foulger | |
| 6,603,192 B2 | 8/2003 | Thomas et al. | |
| 7,138,090 B2 * | 11/2006 | Blok | 422/82.01 |
| 7,501,091 B2 * | 3/2009 | Munoz et al. | 422/50 |
| 2002/0009603 A1 | 1/2002 | McGill et al. | |
| 2002/0065349 A1 | 5/2002 | Manoharan | |
| 2002/0131898 A1 | 9/2002 | Fleischer et al. | |
| 2003/0156290 A1 | 8/2003 | Colvin, Jr. et al. | |
| 2003/0162987 A1 | 8/2003 | Houser et al. | |

FOREIGN PATENT DOCUMENTS

| | | |
|---|---|---|
| EP | 0373941 | 6/1990 |
| JP | 11043556 | 2/1999 |
| JP | 2001116686 | 4/2001 |
| JP | 2003012938 | 1/2003 |
| JP | 2003166170 | 6/2003 |
| WO | WO 92/10528 | 6/1992 |
| WO | WO 01/88042 | 11/2001 |

(Continued)

OTHER PUBLICATIONS

"Luminescence Quenching in Polymer/Filler Nanocomposite Films Used in Oxygen Sensors," Lu, X., and Winnik, M. A., *Chem. Mater.* 2001, 13, pp. 3449-3463.

(Continued)

*Primary Examiner*—Sam P Siefke
(74) *Attorney, Agent, or Firm*—Price, Heneveld, Cooper, DeWitt & Litton LLP (57) ABSTRACT

A chemical sensor having a transducer element and a layer of composite material including a polymer matrix and a solid particulate filler disposed in the polymer matrix provides chemical sensors exhibiting improved properties. In particular, the device allows polymer matrix materials to be selected based primarily on diffusion properties, strength, stability and other physical characteristics substantially independent of limitations and compromises that arise when attempting to synthesize polymers having specific types of sensory groups chemically bound to the polymer. The invention also allows greater ability to modify sensor response characteristics by appropriate modification of the particulate filler, whereby a diverse sensor array may be fabricated more easily and at a lower cost.

4 Claims, 3 Drawing Sheets

(1)

FOREIGN PATENT DOCUMENTS

WO    WO 02/099822    12/2002

OTHER PUBLICATIONS

"Template Synthesis and Characterization of Layered Al- and Mg-Silsesquioxanes," Ukrainczyk, L., Bellman, R. A., and Anderson, A. B., *J. Phys. Chem. B*, 1997, 101, pp. 531-539.

"X-ray Characteristics of Polyethylene Polyhedral Oligomeric Silsesquioxane Copolymers," *Macromolecules* 2002, 35, pp. 2375-2379.

"A Novel Metallopolymer Nanocomposite Chemical Sensor," Lou Jianzhong; Ariarugirl, Girish; Sankar, Jag. *Polymeric Materials Science and Engineering* (2003), 89 655, CODEN: PMSEDG ISSN: 0743-0515, Abstract only, one page.

"A Novel Metallopolymer Nanocomposite Chemical Sensor," Lou Jianzhong; Ariarugirl, Girish; Sankar, Jag. *Abstracts of Papers*, 226th ACS National Meeting, New York NY, United States, Sep. 7-11, 2003, PMSE-392, Abstract only, one page.

"Example: Polypropylene (isotactic) with 10% Octamethyl-POSS,"Schwab, et al., *Polymer Preprints* 2001, 42, 48, two pages.

\* cited by examiner

FUNCTIONALIZED PARTICLES FOR COMPOSITE SENSORS

FIELD OF THE INVENTION

This invention relates to chemical sensing devices, and more particularly to the use of composite materials for sensing chemical vapors.

BACKGROUND OF THE INVENTION

Chemical vapor sensing instruments are expected to become increasingly important in a variety of applications, including industrial hygiene, environmental clean-up, national defense and homeland security. Improved technology to reliably detect and identify potentially toxic or explosive volatile organic compounds is critically needed for these applications.

Many different approaches are being developed and refined throughout the academic, government and industrial/commercial research and development organizations. Current efforts have focused primarily on improving the portability of traditional analytical instruments such as gas chromatographs and optical spectrometers, and improving the sensitivity and reliability of array-based chemical sensors that measure gravametric, optical or electromechanical properties. The array-based chemical sensors are favored when low cost, portability, ease of operation and ease of maintenance are desired.

A sealed-deployable sensor system must be able to unambiguously detect an analyte of concern and provide an accurate measurement of the analyte of concern regardless of the presence of chemically similar interfering compounds. The most successful field-deployable sensor systems utilize cross-reactive chemical sensor arrays in which individual sensing elements are coated with materials that respond to broad classes of chemical vapors, with each sensor material being chosen to be sufficiently different from the other sensor materials so that the collective array of sensors will span a broad range of possible chemical properties.

A variety of organic, inorganic and organometallic materials have been tested as sensor materials. Notable examples include self-assembled monolayers, Langmuir-Blodgett films, clathrates, small organic molecules and polymers. Most functional commercial and/or prototype vapor sensing instruments use arrays of polymer-coated sensing elements. This is because polymer coatings can be selected to exhibit excellent sorptive properties for organic vapors, rapid diffusion if the polymer is above its glass-to-rubber transition temperature, reversible responses, and linear sorption isotherms over a large concentration range for low polarity vapors. The sensor coating materials may be selected to achieve a wide range of selectivities, such as by synthetic variation of the polymer structure.

In addition to the above properties, it is highly desirable that sensor-coating materials possess excellent processing characteristics. Specifically, mass production of reliable and inexpensive vapor sensing devices will require sensor-coating materials that are readily processable into thin, adherent films.

There are many polymers available that meet many of these requirements and offer other advantages. In particular, polymers can be made with a wide variety of functional groups (e.g., sensing groups) that may be incorporated directly into the polymer backbone during synthesis or appended to the polymer backbone after synthesis. Polymers may also be selected for a particular application based on appropriate molecular compositions and/or molecular architectures. Polymers may also be chosen based on the ability to cross-link, graft to substrates, or both. Many types of polymers are amorphous, i.e., either not crystalline or partially crystalline. Such polymers tend to be either rubbery or glassy and exhibit absorptive properties that may be advantageously employed for vapor sensing applications. Another advantage with using polymers for vapor sensing applications is that many polymers exhibit excellent stability and very low volatility at ambient conditions and/or elevated temperatures. Further, most polymers are easily processed into a variety of different forms. However, it is not easy to develop a simple polymer that will exhibit a combination of all these desired properties.

It is generally necessary and desirable to use an array of different sensors in a vapor-sensing device since it is impossible to achieve perfectly selective detection of any particular analyte using a single sensor. Any particular sensor will typically respond to several different analytes. However, any given sensor may respond to a particular set of analytes including some, but not all, of the analytes detectable by another sensor. Using a suitable array of sensors, it is possible to identify a single analyte based on a determination of the particular sensors in the array that respond to the analyte. By employing suitable calibration techniques, it may be possible to achieve quantitative analysis for a single analyte, and qualitative or quantitative analysis for a plurality of different analytes.

While vapor sensing devices employing an array of different sensors are generally required to achieve highly selective detection, it is desirable to use only a few different types of base polymers, and more preferably a single type of base polymer, for each of the sensors in the array, and modify the individual members of the array with different functional groups (sensing groups) to achieve a desired array of selective responses. This provides a simplified production process as compared with using a completely different polymer for each member of the array. However, polymers with every conceivable type of functional group are generally commercially unavailable. For example, polymers with hydrogen bond acidic functionalities, which would be useful for selective detection of hydrogen bond basic analytes such as chemical warfare nerve agents and explosives, and which otherwise meet the requirements for polymer detectors, are generally commercially unavailable.

There are currently three common categories of commercially available chemical vapor sensing devices utilizing polymer-coated sensing elements. A first category is devices comprising an array of acoustic wave sensors using quartz crystal microbalances (QCM), surface acoustic wave (SAW) devices, or flexural plate wave (STW) devices as the sensing transducers. For acoustic wave sensors, the generated signals are proportional to the mass of the vapor sorbed by each polymer coating on the surfaces of the device. A second category of commercially available array-based chemical sensors utilizes a chemiresistor transducer comprising an insulating polymer that is loaded with electrically conductive particles. In this device, vapor sorption swells the insulating polymer and increases the resistance through the polymer-conducting particle composite. Lastly, the third common category of commercially available array-based chemical sensors employs a sorbent polymer as the matrix for fluorescent dyes, such as Nile red. Vapor sorption alters the fluorescence signal from the incorporated dye molecules. In a minor variation of this, arrays have been prepared with various dyes in various polymers on the ends of fiber-optic bundles. It is also conceivable that a chemical vapor sensing apparatus could employ any combination of these three types of sensors.

The task of choosing and optimizing a chemically diverse array of polymer-coated sensing elements can be rationally accomplished through the use of solubility interactions and linear solvation energy relationships. It is believed that a sorbent polymer-based sensor array will collect the most chemical information if the polymer coatings in the array cover the full range of solubility interactions, including dispersion, dipole-dipole, and hydrogen-bond interactions. This approach requires a variety of different polymer coatings, including non-polar, polarizable, dipolar, hydrogen bond basic, and hydrogen bond acidic. Many polymer coatings exhibiting these types of solubility interactions are well known and commercially available, with the notable exception of the hydrogen bond acidic polymers. This presents a problem for at least two critically important applications for chemical vapor sensing apparatuses employing polymer-coated sensing elements. In particular, there is a need for the development of hydrogen bond acidic polymer-coated sensors for detection of nerve agents and explosives. In addition, there is a need for the development of hydrogen bond acidic polymer coatings to expand the chemical diversity of a sensor array, thus helping to optimize its ability to discriminate between various classes of vapors.

A large body of research on surface acoustic wave devices has demonstrated that incorporation of highly fluorinated alcoholic or phenolic functional groups into the sensing polymers is an effective way of maximizing hydrogen bond acidity. Concomitant minimization of basicity reduces the extent and strength of self-association, which would otherwise tend to lessen the driving force for interaction with basic vapors. Self-association is a major drawback to the use of carboxylic acid functional groups, which are good hydrogen-bond acids as monomers, but nearly always self-associate when in a condensed phase.

Strongly hydrogen bond acidic polymers also have intrinsically high polarity. Although this is a desirable feature in terms of chemical sensitivity, it poses a potential problem because highly polar function groups on polymers lead to higher glass-to-rubber transition temperatures than those of corresponding nonpolar polymers. Polymers having a glass-to-rubber transition temperature near or above room temperature (about 22° C.) typically act as diffusion barriers and provide unacceptably slow response times when used as coatings for chemical sensors.

SUMMARY OF THE INVENTION

The invention provides composite chemical sensing materials that exhibit excellent mechanical properties, and more strength and better aging performance than conventional polymer sensor materials in which the sensor groups are part of the chemical structure of the polymer. The chemical sensing composite materials of this invention include a matrix polymer having a low glass transition temperature, typically at or below room temperature (about 22° C.), and exhibit good diffusion properties and good response times on contact with chemical vapors. The chemical sensing composite materials of this invention include a polymer matrix, and functionalized solid particles dispersed in the polymer matrix.

An advantage of the invention is that it allows the polymer matrix to be selected based primarily on its diffusion properties, strength, stability and other physical characteristics, independent of limitations and compromises that arise when attempting to synthesize polymers having specific types of sensory groups chemically bound to the polymer. Another advantage is that a single polymer matrix or relatively few different polymer matrices may be used to prepare a diverse sensor array using different fillers. Also, the ability to modify a solid particulate to produce a variety of different types of sensory filler materials allows certain types of sensors to be fabricated more easily and at a lower cost.

These and other features, advantages and objects of the present invention will be further understood and appreciated by those skilled in the art by reference to the following specification, claims and appended drawings.

DETAILED DESCRIPTION OF THE PREFERRED EMBODIMENTS

The term "composite" as used herein refers to a composition comprising at least two distinct immiscible phases, including a continuous phase or matrix, and a dispersed phase. These distinct phases distinguish the composite from a solution which is free of distinct phases and immiscible components. The expression "solid particulate filler" as used herein refers to a dispersed phase that is a solid material at normal ambient conditions.

The matrix used for preparing the composite sensor coatings of this invention preferably include a polymer having a relatively low glass transition temperature, i.e., a glass transition temperature that is preferably at about room temperature (22° C.) or below room temperature. The matrix polymer may have any molecular architecture. Suitable matrix polymers include linear polymers, branched polymers, hyperbranched polymers, combburst polymers, dendrons, dendrimers, cross-linked polymers, etc. Specific examples of suitable matrix polymers include, but are not limited to, linear, branched and hyperbranched polycarbosilanes, polycarbosiloxanes, polycarbosilazenes, and polysiloxanes.

The functionalized particles dispersed in the polymer matrix may be prepared from solid particulates of the type generally referred to as fillers. Examples of suitable functionalizable particles include various clays, synthetic fibers such as nylon fibers, aluminum hydroxide, calcium silicate, zinc oxide, carbon fiber, glass fiber, silica, alumina, alumina-silica, carbon black, carbon nanotubes, fullerene, silsesquioxanes, and the like. Each of these materials has hydroxyl or other functional groups that can be reacted with a molecule having a sensory moiety to form a functionalized sensory particle that may be dispersed in a polymer matrix. The solid particles or fillers used in this invention may have an average particle size in the range from about one nanometer to several hundred micrometers. However, smaller particles are preferred, particularly those in the range from about 1 nm to about 1000 nm, in order to achieve better, more uniform dispersion of the particles in the matrix.

Preferred solid filler particles for use in the invention include polyhedral oligomeric silsesquioxanes (POSS). The POSS particles have a rigid, closed-cage siloxane (SiO) structure. Methods of preparing various POSS structures are well known. For example, polyhedral oligomeric silsesquioxanes having hydridosilyl (SiH), vinyl, allyl, thiol, amine, haloalkyl, and other reactive functional groups are commercially available and/or described in the literature. These reactive functional groups may be reacted with various compounds having sensory functional groups to form sensory group functionalized solid particles that are capable of being uniformly dispersed in a polymer matrix.

The term "silsesquioxane" is used herein to describe a large family of substances including fully-condensed silsesquioxane frameworks (i.e., those without any remaining hydrolyzable groups) and incompletely-condensed frameworks having reactive Si—OH groups which are potentially capable for forming additional Si—O—Si linkages via elimination of water. The term "silsesquioxane" is also used herein to describe heterosilsesquioxanes derived by substitution of a main-group, transition-metal or f-element atom for one or more of the silicon atoms in a silsesquioxane. Heterosilsesquioxanes derived by substitution of a metal atom for one or more of the silicon atoms in a silsesquioxane are also referred to as metallasilsesquioxanes. The silsesquioxanes exhibit very good dispersion properties on account of their relatively small particle size, typically from about 5 nm to about 10 nm.

Another advantage with the polyhedral oligomeric silsesquioxanes is that they have a very high ratio of functional groups to mass.

Various chemistries may be utilized for functionalizing the solid filler particles. For example, hydrosilylation reactions may be employed by reacting a vinyl or allyl functionalized polyhedral oligosilsesquioxane and/or heterosilsesquioxane with a hydrido-silane or hydrido-siloxane functionalized compound that also has a sensory functional group or by reacting a hydridosilane POSS with a vinyl or allyl compound containing a sensory functional group. Vinyl and/or allyl functionalized polyhedral oligosilsesquioxanes are commercially available or may be synthesized by techniques known in the art. As another example, Michael addition reactions may be employed by reacting a commercially available silsesquioxane having methylcarboxyl groups with a compound having an amine group and at least one sensory group. Further, functional groups on the solid particles, such as polyhedral oligomeric silsesquioxanes, silica, etc., may be reacted with various linking compounds having at least one functional group that will react with a functional group on the solid particle and at least one other functional group that can be reacted with a compound having a sensory moiety. Examples of functional groups that may be utilized for linking the solid particles with a compound having a sensory group include hydroxyl, thiol, carboxyl, ester, alkoxy, alkenyl, allyl, vinyl, amino, halo, urea, oxiranyl, aziridinyl, oxazolinyl, amidazolinyl, sulfonato, phosphonato, hydrosilyl, isocyanato, isothiocyanato, and others.

Fullerenes, carbon nanotubes, and the like may be functionalized by reaction of their carbon-carbon double bonds with various sensor-bearing species. Glass fiber, silica, and the like have surface SiOH groups which can be converted to sensor groups, such as by reaction with a variety of commercially available coupling agents of the form $(RO)_xR'_{3-x}Si(CH_2)_yX$, where SiOR reacts with SiOH, x is zero, 1, 2 or 3, y is a positive integer, and X is a functional group such as (an epoxy, amine, acrylate, isocyanate, etc.) to which appropriate sensor groups can be attached.

Silicon-containing polymers, including hyperbranched polymers, are particularly useful for use as the matrix polymer for the chemical sensor applications of this invention due to their low glass transition temperature, excellent processability, ease of film formation, inertness and stability. The presence of a high proportion of silicon-carbon and/or silicon-oxygen bonds in the backbone of the silicon-containing polymers imparts very low polarity and very low bias polarity and low glass transition temperature. The silicon-containing polymers may be easily prepared using hydrosilylation chemistry for polymer synthesis and, if desired, for subsequent cross-linking.

The matrix polymer may include chemically sensitive functional groups (sensory groups) that are the same as those on the sensory functionalized solid particulate fillers distributed through the polymer matrix, i.e., both the matrix polymer and the particulate filler may include the same sensing group that responds to a particular analyte of interest. Alternatively, the matrix polymer may be inert to the analyte of interest, with only the functionalized solid particulate filler responding to the analyte.

The sensory groups linked to the solid particulate filler, and optionally to the matrix polymer, may be selected from a wide variety of functional groups that are commonly employed for detecting analytes of interest. Examples of sensory functional groups that may be bound to the solid particulate fillers include silanol, dihydroxypyrimidine, hydantoin, phenols, halogenated alcohols, oxime, boronic acid, thioxamide, thiol, and succinimide groups.

Chemically sensitive (sensory) functional groups are functional groups that are capable of interacting with an analyte of interest (e.g., a chemical vapor). Interaction of the functional groups with the analyte results in a change in a measurable property or characteristic (e.g., electrical resistance, mass, etc.) of the composite material. Such interactions include chemical bonding, dipole-dipole interactions, chemical adsorption, physical adsorption, and the like.

Preferred chemically sensitive functional groups include hydrogen bond acidic groups such as phenolic and alcoholic alkyl(hydroxy alkyl) groups, especially fluorinated phenols and fluorinated alcoholic alkyls. Hydrogen bond acidic functional groups play an important role in the detection of certain analytes, particularly nerve agents and explosives. Further, hydrogen bond acidic functional groups are important to optimizing the chemical diversity of an array of polymer coated sensing elements. Other preferred sensory functional groups include hydrogen bond basic groups such as amine, ether, cyano (CN), nitrogen and oxygen heterocycles (e.g., pyridine, pyrimidine, pyrrole, furan, and others), groups containing phosphorous-oxygen double bonds (e.g., phosphonates), moieties containing sulfoxide (—S=O) groups, moieties containing sulfone (—S)=$O_2$ groups, moieties containing nitroso (NO) groups, and moieties containing nitro ($NO_2$) groups.

Chemical sensors prepared in accordance with an aspect of this invention comprise a composite sensory or detector material which includes a polymer matrix and sensory functionalized solid particulate filler material dispersed throughout the matrix. The composite sensory material is utilized in combination with a transducer element that is capable of detecting a change in the composite material due to an interaction with an analyte and generating a signal to indicate the change.

Suitable transducers include any device or mechanism that is capable of detecting any change in a physical (e.g., mass, electrical resistance, etc.), chemical (e.g., color change), or physical-chemical property of the coating material due to interaction of the coating material with an analyte and providing a signal indicative of the interaction, and hence indicating the presence and/or quantity of analyte contacting the composite sensory material. Suitable transducer elements include, but are not limited to, quartz crystal microbalance, surface acoustic wave devices, flexural plate wave devices, chemiresistor transducers, and colorimetric transducers.

In general, the composite sensory materials of this invention are prepared by uniformly dispersing a sensory functionalized solid particulate filler material in the polymer matrix material. This can be achieved using any suitable technique, such as melt blending or homogeneously mixing the functionalized solid particulate filler materials with monomers, other liquid phase polymer precursors, or polymers, and subsequently curing or otherwise solidifying the monomers or polymer precursors to form a polymer matrix.

The composite sensor materials of the invention may be coated onto a surface of a transducer element such as a quartz crystal microbalance or surface acoustic wave device using conventional coating techniques, such as spray coating, dip coating, brushing, spin coating, solvent casting, etc. In addition to the previously mentioned coating techniques, the composite sensory materials of this invention may be applied to a substrate by various other methods selected from, but not limited to, chemical vapor deposition, vacuum deposition, solution casting, micro- and sub-micro-emulsion spritzing, rapid expansion of super critical fluids, pulsed laser evaporation, matrix assisted pulsed laser evaporation, etc. Examples of other devices on which the composite sensory materials of this invention may be coated include optical waveguide devices, optical fiber-based devices, dip-in or apply-to test kits, etc.

The amount of sensory functionalized solid particulate filler material utilized in the composites of this invention may vary greatly depending on a variety of factors, including the analyte or analytes to be detected, the type of transducer utilized, the characteristics of the matrix polymer, the particular type of sensory groups bound to the solid particulate filler, and the characteristics of the solid particulate filler. In general, the amount of sensory functionalized solid particulate filler material utilized in the composites of this invention are selected to achieve an optimal balance between response sensitivity (which increases with higher filler loading) and diffusive properties (which tend to diminish with higher filler loading). However, suitable filler loadings tend to be in a range from about 5% by weight to about 50% by weight, and more typically from about 10% to about 25% by weight.

The composites of this invention exhibit improved mechanical properties as compared with conventional sensor materials, including better strength properties and better aging performance (i.e., long term retention of mechanical and sensing properties). The composites of this invention also allow lower cost production of a variety of different sensor types (i.e., sensors responsive to different analytes) using the same matrix polymer with different functionalized fillers.

The invention is further illustrated by the following non-limiting examples.

EXAMPLES

Example 1

Polymethylphenylcarbosilane-C6 (1) Matrix Polymer

Figure 1:
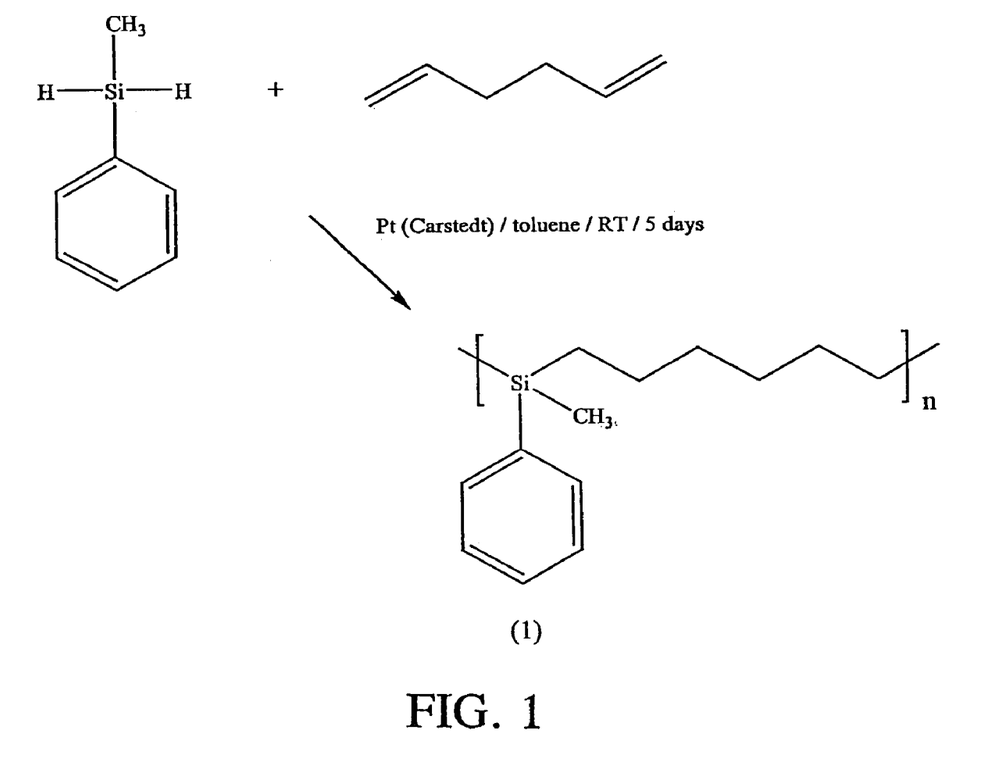
FIG. 1 is a reaction scheme showing synthesis of the polymethylphenylcarbosilane of Example 1.

A 25 mL one-necked round-bottomed flask was equipped with a Teflon coated magnetic stirrer bar and a condenser with a nitrogen inlet at its top. The flask was charged with 1.647 g methylphenylsilane (13.4 mmol), 1.107 g 1,6-hexadiene (13.4 mmol), 10 mL toluene and one drop of platinum divinyltetramethyldisiloxane complex in xylene. The mixture was stirred at room temperature for 5 days and then stirred with activated charcoal at room temperature for 24 hours. The charcoal residue was removed by gravity filtration and the toluene was evaporated to give the polymeric product (synthesized in accordance with the reaction scheme shown in FIG. 1) as an oil in quantitative yield. $^1$H NMR (CDCl$_3$): δ (ppm) 0.23 (s; SiCH$_3$), 0.73 (m; SiCH$_2$), 1.27-1.35 (2 m; SiCH$_2$CH$_2$, Si(CH$_2$)$_2$CH$_2$), 7.34 (m; ArH), 7.48 (m; ArH). $^{13}$C NMR (CDCl$_3$): δ (ppm) −5.1 (SiCH$_3$), 14.1 (SiCH$_2$), 23.7 (SiCH$_2$CH$_2$), 33.2 (Si(CH$_2$)$_2$CH$_2$), 127.6 (ArC), 128.6 (ArC), 133.8 (ArC), 138.9 (ArCSi). GPC (THF as elutant): $M_w$=15875, $M_n$=10205, polydispersity=1.56. DSC; $T_g$=−49° C.

Example 2

Octa-[Propyl-(Bis(-4-Hydroxyphenyl)Hexafluoropropane)] POSS (2)

Figure 2:
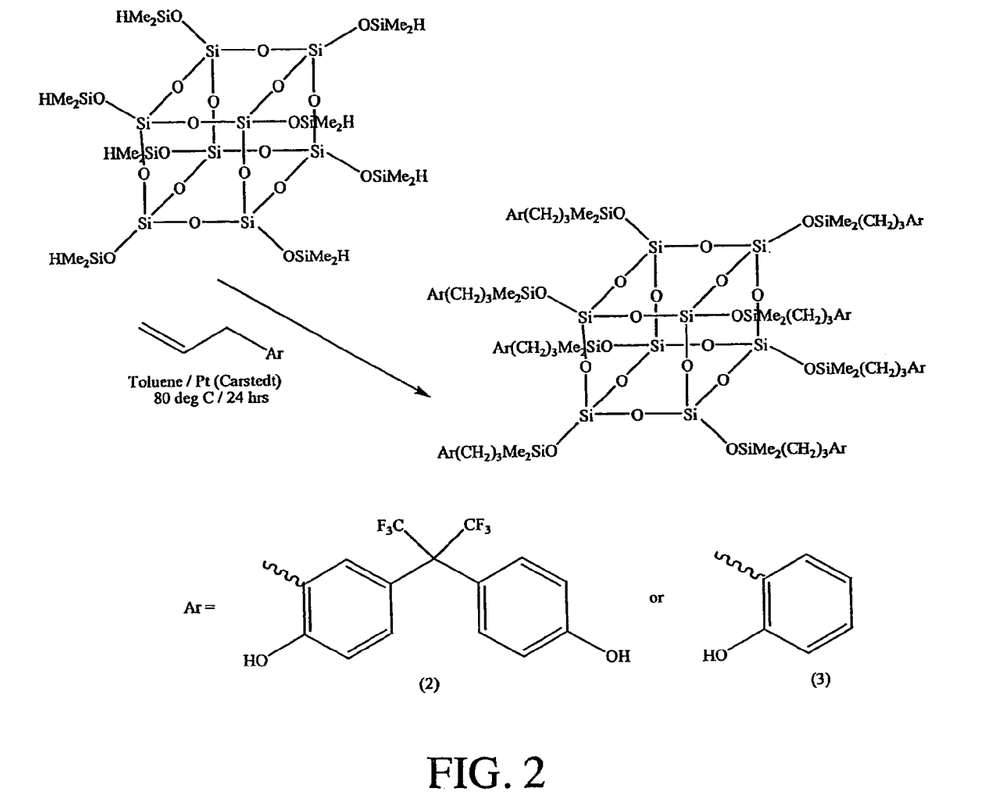
FIG. 2 is a reaction scheme showing preparation of the octa-[propyl-(bis(-4-hydroxyphenyl)hexafluoropropane)] POSS (2) of Example 2.

A 10 mL one-necked round-bottomed flask was equipped with a Teflon coated magnetic stirrer bar and a condenser with a nitrogen inlet at its top. The flask was charged with 0.070 g octasilane-POSS (0.069 mmol), 0.208 g 2-(3-allyl-4-hydroxyphenyl)-2-(4-hydroxyphenyl)hexafluoropropane (8 equivalents, 0.552 mmol), 4 mL toluene and one drop of platinum divinyltetramethyldisiloxane complex in xylene. The mixture was heated at 80° C. for 24 hours and then stirred with activated charcoal at room temperature for 24 hours. The charcoal residue was removed by gravity filtration and the toluene was evaporated to give the product (synthesized in accordance with the reaction scheme shown in FIG. 2) as a white solid in quantitative yield. IR (thin film): ν (cm$^{-1}$) 3406 (OH), 2959, 2926, 2869 (CH$_2$), 1611 (Ar), 1513 (Ar), 1436 (Ar), 1380 (CF$_3$), 1253 (SiCH$_3$), 1204 (SiCH$_2$), 1168, 1090 (SiOSi). $^1$H NMR (CDCl$_3$): δ (ppm) 0.10 (s; SiCH$_3$), 0.88-0.94 (t; SiCH$_2$), 1.83-1.88 (m; SiCH$_2$CH$_2$), 2.54-2.56 (t; ArCH$_2$) 6.79-6.82 (m; ArH), 6.97-7.00 (m; ArH), 7.06 (s; ArH). $^{13}$C NMR (CDCl$_3$): δ (ppm) 1.0 (SiCH$_3$), 18.1 (SiCH$_2$), 29.7 (SiCH$_2$CH$_2$), 33.3 (ArCH$_2$), 114.9, 122.3, 125.3, 128.2, 129.1, 131.7, 137.9 (ArC, CF$_3$, C(CF$_3$)$_2$). MALDI-TOF MS (dihydroxybenzoic acid matrix): m/z 4087 (Calc. 4026), 3711 (Calc. 3650).

Example 3

Octa[Propyl-2-Phenol] POSS (3)

A 10 mL one-necked round-bottomed flask was equipped with a Teflon coated magnetic stirrer bar and a condenser with a nitrogen inlet at its top. The flask was charged with 0.200 g octasilane-POSS (0.196 mmol), 0.210 g 2-allylphenol (8 equivalents, 1.57 mmol), 3 mL toluene and one drop of platinum divinyltetramethyldisiloxane complex in xylene. The mixture was heated at 80° C. for 24 hours and then stirred with activated charcoal at room temperature for 24 hours. The charcoal residue was removed by gravity filtration and the toluene was evaporated to give the product as a white solid in quantitative yield. IR (thin film): ν (cm$^{-1}$) 3444 (OH), 2954, 2924, 2861 (CH$_2$), 1590, 1505, 1486, 1449 (Ar), 1250 (SiCH$_3$), 1172, 1087 (SiOSi). $^1$H NMR (CDCl$_3$): δ (ppm) 0.12 (s; SiCH$_3$), 0.64-0.70 (t; SiCH$_2$), 1.62-1.76 (m; SiCH$_2$CH$_2$), 2.59-2.64 (t; ArCH$_2$) 6.73-7.33 (4 m; ArH). $^{13}$C NMR (CDCl$_3$): δ (ppm) 1.2 (SiCH$_3$), 17.6 (SiCH$_2$), 23.5 (SiCH$_2$CH$_2$), 33.6 (ArCH$_2$), 115.5 (ArCH), 121.0 (ArCH), 127.2 (ArCH), 128.6 (ArCH), 130.5 (ArCCH$_2$), 138.1 (ArCOH). $^{29}$Si NMR (CDCl$_3$): δ (ppm) 15.6 (OSiMe$_2$CH$_2$). MALDI-TOF MS (2,4,6-trihydroxyacetophenone monohydrate matrix): m/z 2117 (Calc. 2090).

Example 4

Mono-[1-(4-Hydroxy-4-Trifluoromethyl-5,5,5-Trifluoro)Pentene] Hepta(Isobutyl) POSS (4)

Figure 3:
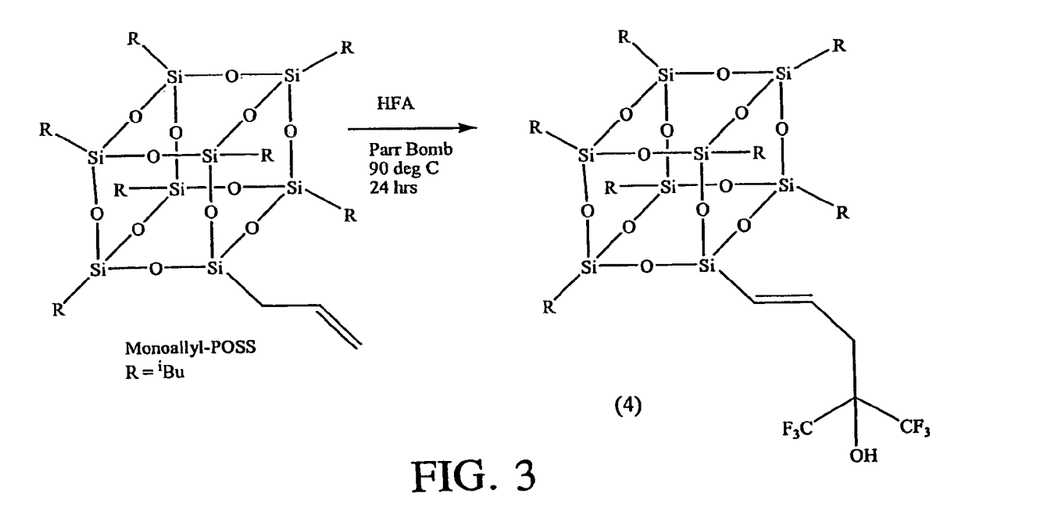
FIG. 3 is a reaction scheme showing preparation of the mono-[1-(4-hydroxy-4-trifluoromethyl-5,5,5-trifluoro)pentene]hepta(isobutyl) POSS (4) shown in Example 4.

A 300 mL steel Parr bomb reactor with a glass liner was charged with 0.28 g monoallyl isobutyl POSS (0.327 mmol). The reactor was purged and then charged with 17.73 g hexafluoroacetone (0.106 mol, approximate 300-fold excess). After 24 hours at 90° C. excess hexafluoroacetone was pumped out of the reactor and destroyed by bubbling through an appropriate quantity of sodium borohydride solution in triglyme. The product (prepared as shown in FIG. 3) was isolated by removal from reactor. IR (thin film): $\nu$ (cm$^{-1}$) 3600 (free OH), 3489 (hydrogen-bonded OH), 2956, 2911, 2867 (CH$_2$), 1379 (CF$_3$), 1279, 1209, 1146, 1054 (SiCH$_2$) $^1$H NMR (CDCl$_3$): $\delta$ (ppm) 0.58-0.63 (m; SiCH$_2$), 0.92-0.95 (d; CHCH$_3$), 1.78-1.90 (m; CH(CH$_3$)$_2$), 2.75-2.95 (2 d; SiCH=CHCH$_2$C(CF$_3$)$_2$OH cis and trans), 5.69-6.12 (2 m; SiCH=CHCH$_2$C(CF$_3$)$_2$OH), 6.29-6.48 (2 m; SiCH=CHCH$_2$C(CF$_3$)$_2$ OH). $^{13}$C NMR (CDCl$_3$): $\delta$ (ppm) 22.2, 23.8, 25.6 ($^i$BuC), 33.4 (CH$_2$C(CF$_3$)$_2$OH cis), 37.0 (CH$_2$C(CF$_3$)$_2$OH trans), 117.1-140.9 (septet, C(CF$_3$)$_2$), 129.9 (SiCH=CHCH$_2$ C(CF$_3$)$_2$OH cis), 131.2 (SiCH=CHCH$_2$C(CF$_3$)$_2$OH trans), 139.9 (SiCH=CHCH$_2$C(CF$_3$)$_2$OH trans), 141.2 (SiCH=CHCH$_2$C(CF$_3$)$_2$OH cis). $^{29}$Si NMR (CDCl$_3$): $\delta$ (ppm) −64.1, −64.6 (O$_3$SiCH). MALDI-TOF MS (2,4,6-trihydroxyacetophenone monohydrate matrix): m/z 1059 (Calc. 1024).

Example 5

Mono-Bisphenol-A POSS (5)

Figure 4:
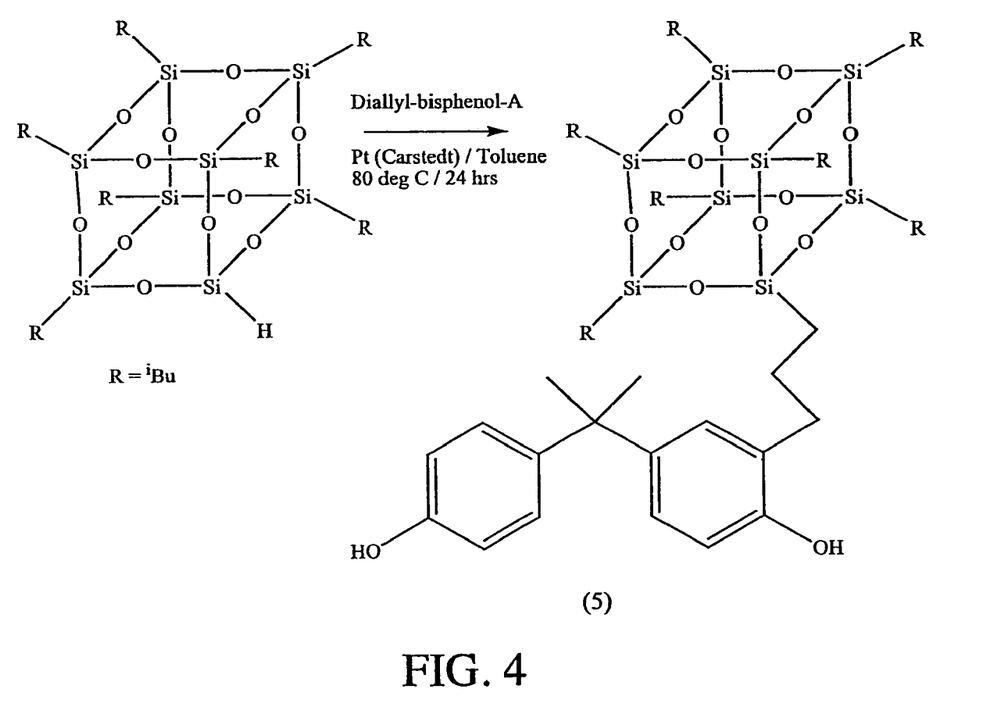
FIG. 4 is a reaction scheme showing preparation of the mono-bisphenol-A POSS (5) of Example 5.

A 100 mL one-necked round-bottomed flask was equipped with a Teflon coated magnetic stirrer bar and a condenser with a nitrogen inlet at its top. The flask was charged with 2.54 g monosilane-POSS (3.11 mmol, 2 equivalents), 0.480 g 2,2'-diallyl bisphenol-A (1.56 mmol, 1 equivalent), 30 mL toluene and one drop of platinum divinyltetramethyl-disiloxane complex in xylene. The mixture was heated at 80° C. for 6 days and then stirred with activated charcoal at room temperature for 24 hours. The charcoal residue was removed by gravity filtration and the toluene was evaporated to give a mixture of three products. The product (prepared as shown in FIG. 4) with the highest OH content was isolated by flash column chromatography (1:2 v/v dichloromethane-hexane, gradient to 100% dichloromethane); 2-(propyl-POSS)-bisphenol-A, 0.24 g product. Rf=0.45 (CH$_2$Cl$_2$). IR (thin film): $\nu$ (cm$^{-1}$) 3615 (free OH), 3541 (hydrogen-bonded OH), 2956, 2926, 2904, 2874 (CH$_2$ and CH$_3$), 2630, 1804, 1605, 1497, 1457, 1398, 1379, 1364, 1327, 1261 (SiCH$_2$), 1228 (SiCH), 1109 (SiOSi), 1036, 836 (SiOSi). $^1$H NMR (CDCl$_3$): $\delta$ (ppm) 0.61-0.66 (m; SiCH$_2$ and iBu), 0.88-1.00 (m; CH$_3$), 1.64 (s; Ar$_2$C (CH$_3$)$_2$), 1.80-1.93 (CH(CH$_3$)$_2$), 2.51-2.57 (t; ArCH$_2$), 6.09-6.22 (m; ArH), 6.82-7.00 (m; ArH), 7.30 (d; ArH). $^{29}$Si NMR (CDCl$_3$): $\delta$ (ppm) −63.0, −61.0 (O$_3$SiCH). MALDI-TOF MS (2,4,6-trihydroxyacetophenone monohydrate matrix): m/z 1129 (Calc. 1085).

Example 6

Initial SAW Responses

Compositions were prepared by uniformly blending the polycarbosilane of Example 1 with each of the four fillers from Examples 2-5 in the amount indicated in the following table. The resulting composites were coated onto a 500 MHz surface acoustic wave (SAW) substrate (transducer element) to form a chemical sensor. The composite surface of the chemical sensors were each exposed to a flowing gas containing 0.5 grams per cubic meter of dimethyl methylphosphonate (DMMP) (a chemical compound commonly employed for testing purposes to simulate a nerve agent) for a period of 5 minutes. The excellent SAW responses are shown in the table. A control experiment in which a SAW substrate was coated with pure polycarbosilane (1) gave no significant SAW response with DMMP vapor.

| Matrix | Filler | SAW response (Hz) |
| --- | --- | --- |
| 85% Polycarbosilane (1) | 15% POSS Compound (2) | 910 |
| 85% Polycarbosilane (1) | 15% POSS Compound (3) | 1294 |
| 80% Polycarbosilane (1) | 20% POSS Compound (4) | 1165 |
| 85% Polycarbosilane (1) | 15% POSS Compound (5) | 1200 |

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A composite material for sensing an analyte, comprising:
    a polymer matrix which includes a polymer selected from polycarbosilanes, polycarbosiloxanes and polycarbosilazenes; and
    a solid particulate filler dispersed in the polymer matrix, the solid particulate filler having functional groups capable of interacting with the analyte, in which the solid particulate filler is a functionalized filler selected from clays, synthetic fibers, aluminum hydroxide, calcium silicate, zinc oxide, glass fiber, silica, alumina and alumina-silica.

2. A composite material for sensing an analyte, comprising:
    a polymer matrix; and
    a solid particulate filler dispersed in the polymer matrix, the solid particulate filler having functional groups capable of interacting with the analyte, wherein the solid particulate filler is functionalized with hydrogen bond acidic groups, wherein the hydrogen bond acidic groups are selected from phenolic and alcoholic alkyl groups, and wherein the solid particulate filler is a functionalized filler selected from clays, synthetic fibers, aluminum hydroxide, calcium silicate, zinc oxide, glass fiber, silica, alumina and alumina-silica.

3. A composite material for sensing an analyte, comprising:
    a polymer matrix; and
    a solid particulate filler dispersed in the polymer matrix, the solid particulate filler having functional groups capable of interacting with the analyte, wherein the solid particulate filler is functionalized with hydrogen bond acidic groups, wherein the hydrogen bond acidic groups are selected from fluorinated phenols and fluorinated alcoholic alkyls, and wherein the solid particulate filler is a functionalized filler selected from clays, synthetic fibers, aluminum hydroxide, calcium silicate, zinc oxide, glass fiber, silica, alumina and alumina-silica.

4. A composite material for sensing an analyte, comprising:
   a polymer matrix; and
   a solid particulate filler dispersed in the polymer matrix, the solid particulate filler having functional groups capable of interacting with the analyte, wherein the solid particulate filler is functionalized with hydrogen bond basic groups, wherein the hydrogen bond basic groups are selected from amine groups, ether groups, cyano groups, nitrogen and oxygen heterocyclic groups, groups containing phosphorous-oxygen double bonds, groups containing a sulfoxide moiety, groups containing a sulfone moiety, groups containing a nitro moiety, and groups containing a nitroso moiety, and wherein the solid particulate filler is a functionalized filler selected from clays, synthetic fibers, aluminum hydroxide, calcium silicate, zinc oxide, glass fiber, silica, alumina and alumina-silica.

* * * * *